US010272657B2

(12) United States Patent
Yu et al.

(10) Patent No.: US 10,272,657 B2
(45) Date of Patent: Apr. 30, 2019

(54) METHOD FOR MICROPATTERNING A SUBSTRATE AND A PATTERNED SUBSTRATE FORMED THEREOF

(75) Inventors: Haiyang Yu, Singapore (SG); Lay Poh Tan, Singapore (SG)

(73) Assignee: Nanyang Technological University (SG)

( * ) Notice: Subject to any disclaimer, the term of this patent is extended or adjusted under 35 U.S.C. 154(b) by 576 days.

(21) Appl. No.: 13/881,000

(22) PCT Filed: Oct. 25, 2011

(86) PCT No.: PCT/SG2011/000375
§ 371 (c)(1),
(2), (4) Date: Jul. 3, 2013

(87) PCT Pub. No.: WO2012/057706
PCT Pub. Date: May 3, 2012

(65) Prior Publication Data
US 2013/0273337 A1    Oct. 17, 2013

Related U.S. Application Data

(60) Provisional application No. 61/406,385, filed on Oct. 25, 2010.

(51) Int. Cl.
*C03C 15/00* (2006.01)
*C03C 25/68* (2006.01)
(Continued)

(52) U.S. Cl.
CPC ............ *B32B 37/025* (2013.01); *A61L 27/50* (2013.01); *B32B 38/10* (2013.01);
(Continued)

(58) Field of Classification Search
CPC .............................. B32B 37/025; B32B 38/10
(Continued)

(56) References Cited

U.S. PATENT DOCUMENTS 3,918,895 A * 11/1975 Mizuno .................. D06P 5/003
101/470
6,808,364 B2   10/2004 Jeans
(Continued)

FOREIGN PATENT DOCUMENTS

WO    WO 2000/000177      1/2000
WO    WO 2004/027460      4/2004
(Continued)

OTHER PUBLICATIONS

Abdel-Bary et al. (Indian Journal of Textile Research, vol. 5, Jun. 1980, pp. 37-40).*
(Continued)

*Primary Examiner* — Thomas T Pham
(74) *Attorney, Agent, or Firm* — Schiff Hardin LLP

(57) ABSTRACT

A method of micropatterning a substrate is provided. The method comprises providing a template substrate having a patterned surface inked with a composition of interest; contacting the patterned surface with an intermediate substrate, thereby transferring the composition to the surface of the intermediate substrate; contacting the surface of the intermediate substrate comprising the composition with the substrate; and removing the intermediate substrate by dissolution using a solvent. A patterned substrate formed using the method, as well as a biosensor comprising the patterned substrate is also provided.

17 Claims, 11 Drawing Sheets

(51) Int. Cl.
*B32B 37/00* (2006.01)
*A61L 27/50* (2006.01)
*G01N 33/543* (2006.01)
*B32B 38/10* (2006.01)

(52) U.S. Cl.
CPC .... *G01N 33/54393* (2013.01); *A61L 2400/18* (2013.01); *Y10T 428/24802* (2015.01)

(58) Field of Classification Search
USPC .......................................................... 216/54
See application file for complete search history.

(56) References Cited

U.S. PATENT DOCUMENTS

| | | | | |
|---|---|---|---|---|
| 2004/0071836 | A1* | 4/2004 | Chu | A23G 3/28 426/104 |
| 2006/0237390 | A1 | 10/2006 | King et al. | |
| 2006/0292312 | A1 | 12/2006 | Kim et al. | |
| 2007/0098899 | A1* | 5/2007 | Wessels | B41M 3/006 427/256 |
| 2007/0169643 | A1* | 7/2007 | Merrill | B41K 1/02 101/109 |
| 2009/0199960 | A1 | 8/2009 | Nuzzo et al. | |
| 2009/0258006 | A1* | 10/2009 | Weiss | C07K 14/78 424/130.1 |
| 2010/0213169 | A1* | 8/2010 | Hiraoka | B32B 3/02 216/41 |
| 2011/0180906 | A1* | 7/2011 | Wessels | B82Y 10/00 257/618 |
| 2012/0048135 | A1* | 3/2012 | Burberry | B41C 1/05 101/483 |

FOREIGN PATENT DOCUMENTS

| | | |
|---|---|---|
| WO | WO 2007/112878 | 10/2007 |
| WO | WO 2008/115160 | 9/2008 |

OTHER PUBLICATIONS

The Royal Society of Chemistry, 2007.*
Pearson et al. (WO2008032006), Mar. 20, 2008.*
Wikipedia, "Gelatin", Website, no date.*
Liang et al. ("Biomechanical Properties of In Vivo Human Skin From Dynamic Optical Coherence Elastography", IEEE Transactions on Biomedical Engineering, vol. 57, No. 4, Apr. 2010).*
Falconnet, D., et al., "Surface engineering approaches to micropattern surfaces for cell-based assays", Biomaterials, vol. 27, pp. 3044-3063 (2006).
Teixeria, A., et al., "The promotion of neural maturation on soft substrates", Biomaterials, vol. 30, pp. 4567-4572 (2009).
Huang, S., et al., "Shape-Dependent Control of Cell Growth, Differentiation, and Apoptosis: Switching between Attractors in Cell Regulatory Networks", Experimental Cell Research, vol. 261, pp. 91-103 (2000).
Gao, L., et al., "Stem Cell Shape Regulates a Chondrogenic Versus Myogenic Fate Through Rac 1 and N-Cadherin", Stem Cells, vol. 28, pp. 564-572 (2010).
McBeath, R., et al., "Cell Shape, Cytoskeletal Tension, and RhoA Regulate Stem Cell Lineage Commitment", Developmental Cell, vol. 6, pp. 483-495 (2004).
Kumar, A., et al., "Patterning Self-Assembled Monolayers: Applications in Materials Science", Langmuir, vol. 10, pp. 1498-1511 (1994).
Perl, A., et al., "Microcontact Printing: Limitations and Achievements", Advance Materials, vol. 21, pp. 2257-2268 (2009).
Engler, A., et al., "Matrix Elasticity Directs Stem Cell Lineage Specification", Cell, vol. 126, pp. 677-689 (2006).
Engler, A., et al., "Myotubes differentiate optimally on substrates with tissue-like stiffness: pathological implications for soft or stiff microenvironments", The Journal of Cell Biology, vol. 166, No. 6, pp. 877-887 (2004).

Rape, A., et al., "The regulation of traction force in relation to cell shape and focal adhesions", Biomaterials, vol. 32, pp. 2043-2051 (2011).
Suh, K., et al., "Soft Lithographic Patterning of Hyaluronic Acid on Hydrophilic Substrates Using Molding and Printing", Advanced Matters, vol. 16, No. 7, pp. 584-588 (2004).
Feinberg, A., et al., "Muscular Thin Films for Building Actuators and Powering Devices", Science, vol. 317, pp. 1366-1370 (2007).
Lötters, J.C., et al., "The mechanical properties of the rubber elastic polymer polydimethylsiloxane for sensor applications", J. Micromech. Microeng., vol. 7, pp. 145-147 (1997).
Yeong, W., et al., "Multiscale Topological Guidance for Cell Alignment via Direct Laser Writing on Biodegradable Polymer", Tissue Engineering: Part C, vol. 16, No. 5, pp. 1011-1021 (2010).
Mata, A., et al., "Growth of connective tissue progenitor cells on microtextured polydimethylsiloxane surfaces", J. Biomed. Mater. Res., vol. 62, pp. 499-506 (2002).
Libioulle, L., et al., "Contact-Inking Stamps for Microcontact Printing of Alkanethiols on Gold", Langmuir, vol. 15, pp. 300-304 (1999).
Panyam, J., et al., "Biodegradable nanoparticles for drug and gene delivery to cells and tissue", Advance Drug Delivery Reviews, vol. 55, pp. 329-347 (2002).
Christman, K., et al., "Nanopatterning proteins and peptides", Soft Matter, vol. 2, pp. 928-939 (2006).
Hahn, M., et al., "Laser Scanning Lithography for Surface Micropatterning on Hydrogels", Advanced Materials, vol. 17, pp. 2939-2942 (2005).
Wilbur, J., et al., "Lithographic Molding: A Convenient Route to Structures with Sub-Micrometer Dimensions", Advanced Materials, vol. 7, No. 7, pp. 649-652 (1995).
Tormen, M., et al., Altenative Lithography: Unleashing the Potentials of Nanotechnology, Chapter 10 (Microcontact Printing Techniques), pp. 181-212 (2003).
Schmidt, G., et al., Altenative Lithography: Unleashing the Potentials of Nanotechnology, Chapter 14 (Application of Microcontact Printing and Nanoimprint Lithography), pp. 271-285 (2003).
Wong, A., et al., "Partitioning microfluidic channels with hydrogel to construct tunable 3-D cellular microenvironments", Biomaterials, vol. 29, pp. 1853-1861 (2008).
Lee, S.-H., et al., "Three-dimensional micropatterning of bioactive hydrolgels via two-photon laser scanning photolithography for guided 3D cell migration", Biomaterials, vol. 29, pp. 2962-2968 (2008).
Jackman, R., et al., "Fabrication of Submicrometer Features on Curved Substrates by Microcontact Printing", Science, vol. 269, pp. 664-666 (1995).
Hidber, P., et al., "Microcontact of Palladium Colloids: Micron-Scale Patterning by Electroless Deposition of Cooper", Langmuir, vol. 12, pp. 1375-1380 (1996).
Tse, J.R., et al., "Preparation of Hydrogel Substrates with Tunable Mechanical Properties", Current Protocols in Cell Biology, Supplement 47, pp. 10.16.1-10.16.16 (2010).
Tay, C.Y., et al., "Micropatterned matrix directs differentiation of human mesenchymal stem cells towards myocardial lineage", Experimental Cell Research, vol. 316, pp. 1159-1168 (2010).
Yu, H., et al., "Mechanical behavior of human mesenchymal stem cells during adipogenic and osteogenic differentiation", Biochemical and Biophysical Research Communications, vol. 393, pp. 150-155 (2010).
Fernandez, J.G., et al., Simultaneous biochemical and topographical patterning on curved surfaces using biocompatible sacrificial molds, Journal of Biomedical Materials Research, vol. 98A, Issue 2, pp. 229-234 (2011).
Volcke, C., et al., "Protein pattern transfer for biosensor applications", Biosensors and Bioelectronics, vol. 25, pp. 1295-1300 (2010).
Kane, R.S., et al., "Patterning proteins and cells using soft lithography", Biomaterials, vol. 20, pp. 2363-2376 (1999).

(56) References Cited

OTHER PUBLICATIONS

Yu, H., et al., "A novel and simple microcontact printing technique for tacky, soft substrates and/or complex surfaces in soft tissue engineering", Acta Biomaterialia, vol. 8, pp. 1267-1272 (2012).

* cited by examiner

FIGURE 4 (Prior Art)
(A)
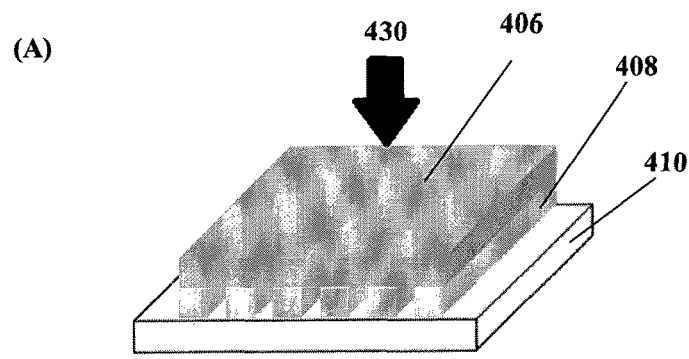
(B)
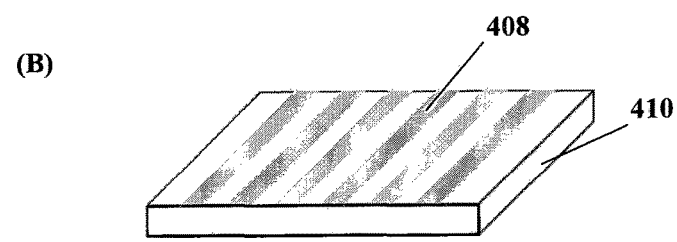
FIGURE 5 (Prior art)
(A)
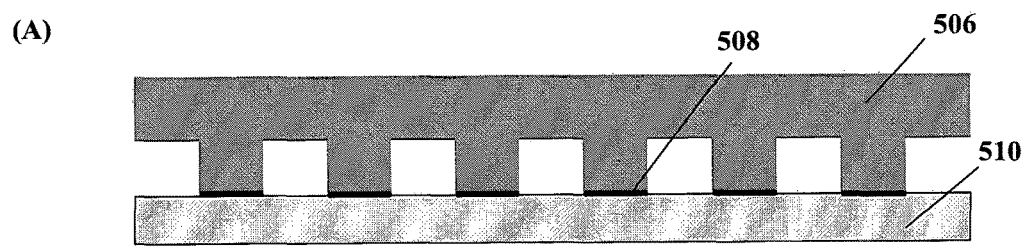
(B)
(C)
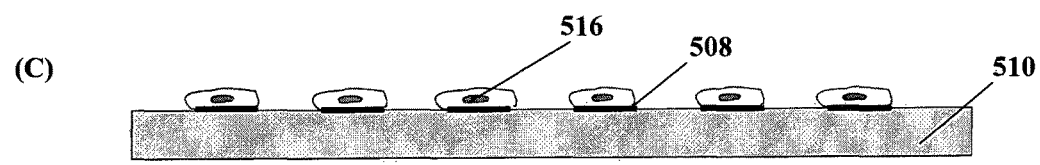

METHOD FOR MICROPATTERNING A SUBSTRATE AND A PATTERNED SUBSTRATE FORMED THEREOF

CROSS-REFERENCE TO RELATED APPLICATIONS

This application makes reference to and claims the benefit of priority of an application for "Novel Method for Micro-Printing on Soft, Sticky and/or Complex Surfaces" filed on Oct. 25, 2010, with the United States Patent and Trademark Office, and there duly assigned Ser. No. 61/406,385. The content of said application filed on Oct. 25, 2010, is incorporated herein by reference in its entirety for all purposes.

TECHNICAL FIELD

The invention relates to a method of micropatterning a substrate and a patterned substrate formed using the method.

BACKGROUND

Various research groups have reported on the close interplay between cell shape and stem cell differentiation. For example, it has been shown that cell shape would affect human mesenchymal stem cells (hMSCs) differentiation, and it has been shown that there is interplay between cell shape and focal adhesion assembly. On these fronts, surface patterning is usually required and micro-contact printing (μCP) remains one of the most popular methods of surface patterning.

Micro-contact printing has gained enormous interests due to its simplicity and wide range of applications in the field of biosensor, cell adhesion, cell differentiation, and biomaterials interaction studies. However, when conventional micro-contact printing is applied to soft and/or tacky substrates, issues like substrate sagging and difficulty in stamp removal leads to non-conformances in the patterns generated. Moreover, it is difficult to apply convention micro-contact printing on non-planar surfaces, and it is almost impossible to apply conventional micro-contact printing on surfaces having complex topographies or wavy surfaces.

While conventional micro-contact printing techniques have been satisfactory in the past, in recent emerging researches involving soft tissue engineering, this technique has proved inadequate. Research has shown that the substrate materials for that stem cells culture have to be mechanically compliant with the soft tissues for soft tissue culture. These materials, such as polydimethylsiloxane (PDMS) and polyacrylamide (PA) gel, having Young's modulus values in the range of 40 kPa or less, can be tacky, which can result in the stamp adhering to the tacky substrates and causing distortion in patterns. These drawbacks become increasingly significant as the substrate used gets softer and tackier.

Moreover, conventional PDMS stamps are relatively stiff to allow ease of handling. Therefore, it is not easy to micro-contact print on surfaces having a complex shape such as cylinder, or spherical scaffolds with curvatures.

In view of the above, there is a need for an improved method to micropattern a substrate. In particular, there is a need for an improved method to micropattern a substrate having a soft and/or sticky surface, as well as objects with surfaces having a complex topography.

SUMMARY OF THE INVENTION

In a first aspect of the invention, a method of micropatterning a substrate is provided. The method comprises a) providing a template substrate having a patterned surface inked with a composition of interest; b) contacting the patterned surface with an intermediate substrate, thereby transferring the composition to the surface of the intermediate substrate; c) contacting the surface of the intermediate substrate comprising the composition with the substrate; and d) removing the intermediate substrate by dissolution using a solvent.

In a second aspect of the invention, a patterned substrate made by a method according to the first aspect is provided.

In a third aspect, a biosensor comprising a patterned substrate according to the second aspect is provided.

In a fourth aspect, there is provided a use of a patterned substrate according to the second aspect of the invention in tissue engineering.

BRIEF DESCRIPTION OF THE DRAWINGS

The invention will be better understood with reference to the detailed description when considered in conjunction with the non-limiting examples and the accompanying drawings, in which:

As shown in FIG. 1A, a liquid pre-polymer 104 is poured on a master template 102. The master template 102 may be formed from silicon. In FIG. 1B, the pre-polymer solution 104 is cured to form a polymer stamp 106 on the master template 102. FIG. 1C shows the structure of the polymer stamp 106 after it has been removed from the master template 102. As can be seen, the polymer stamp 106 has a pattern negative to that of the master template 102. In FIG. 1D, a composition of interest 108 is inked on the polymer stamp 106.

In FIG. 2A, a polymer stamp 206 inked with a composition of interest 208 is contacted with an intermediate substrate 212, thereby transferring the composition 208 to the surface of the intermediate substrate 212 such as that shown in FIG. 2B. A pressure force 230 may optionally be applied to the template substrate. In FIG. 2C, the surface of the intermediate substrate 212 comprising the composition is contacted with a surface of a substrate 210 to transfer the composition 208 to the substrate 210. In FIG. 2D, the intermediate substrate 212 is dissolved with a solvent 214, leaving behind the composition 208 on the substrate 210 as shown in FIG. 2E.

In FIG. 3A, a polymeric stamp 306 inked with a composition 308 is contacted with an intermediate substrate 312, thereby transferring the composition 308 to the intermediate substrate 312. In FIG. 3B, the side of the intermediate substrate 312 comprising the composition 308 is contacted with a substrate 310 to transfer the composition 308 to the substrate 310. In FIG. 3C, the intermediate substrate 312 is dissolved using a suitable solvent 314, leaving behind the composition 308 which is present as a patterned form on the substrate 312 as shown in FIG. 3D. By dissolving the intermediate substrate with a solvent, peeling off of the polymeric stamp 306 after patterning is avoided thereby preventing adherence of the stamp 306 to the substrate 310. In the embodiment shown in the figure, the composition of interest 308 may be protein. In FIG. 3E, cells 316 are seeded on the patterned protein.

FIG. 4 is a schematic diagram of a conventional micro-contact printing procedure. As shown in FIG. 4A, a polymeric mold 406 inked with a compound 408 is contacted directly with a substrate 410, under application of pressure 430. In FIG. 4B, the compound 408 on the mold 406 is transferred to the substrate 410.

FIG. 5 is a schematic diagram of a conventional micro-contact printing (μCP) process. In FIG. 5A, the compound 508 on the mold 506 is transferred to the substrate 510 by direct contact of the substrate 510 with the polymeric stamp 506. In FIG. 5B, the compound 508 is present as a patterned form on the substrate 510. In embodiments in which the compound 508 is a protein, cells 516 may be seeded on the compound 508.

FIG. 6A shows a stamp 606 comprising a composition 608 in direct contact with a soft substrate 610. As depicted in the figure, contact of the stamp 606 with the soft substrate 610 may result in sagging of the substrate 610, in particular, when excessive pressure force is applied to the stamp 606. FIG. 6B depicts the stamp 606 adhering to a tacky substrate 610 when removing the stamp 606 from the substrate surface after printing. In both cases, the patterned composition on the substrate is distorted.

FIG. 9A depicts a strip shape pattern, with each pattern having a dimension of about 40 μm in length, 20 μm in width, and 1 μm in height. FIG. 9B depicts a rectangular shape pattern, with each pattern having a dimension of about 20 μm in length, 2.5 μm in width and 5 μm in height. FIG. 9C depicts a square shape pattern, with each pattern having a dimension of about 5 μm in length, 5 μm in width and 5 μm in height.

FIGS. 10A to 10 C depicts fibronectin (FN) patterned on a PDMS substrate having a Young's modulus of (A) 308 kPa; (B) 12.6 kPa, and (C) 2.1 kPa. FIG. 10D to 10G depicts fibronectin (FN) (D to F) and collagen (COL) (G) patterned on a PDMS substrate surface having features of different sizes and shapes. The scale bar in FIGS. 10A to 10C denotes a length of 100 μm and the scale bar in FIGS. 10D to 10E denotes a length of 50 μm.

FIGS. 15A and 15B are the SEM images of the stamps, while FIGS. 15C and 15D are the patterns created on 1:70 soft and sticky PDMS substrate. The scale bar in the fluorescent images denotes a length of 50 μm.

DETAILED DESCRIPTION OF THE INVENTION

Figure 1:
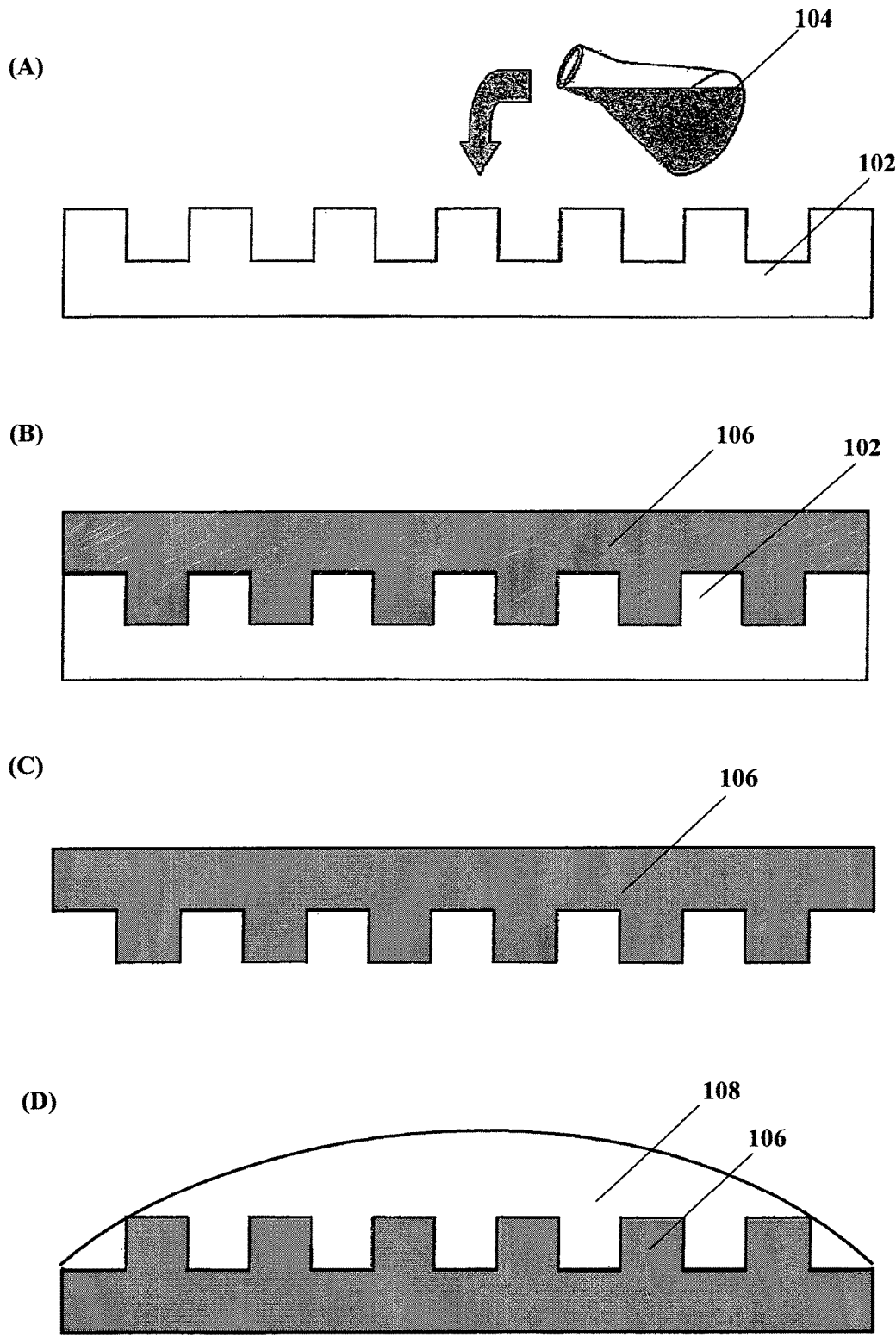
FIG. 1 is a schematic diagram of a general procedure according to various embodiments of the invention to fabricate a template substrate, and subsequent inking of the template substrate with a composition of interest. In the embodiment shown in the figure, the template substrate comprises a polymer.

In a first aspect, the invention refers to a method of micropatterning a substrate. Using a method according to various embodiments of the present invention, substrates, in particular substrates having a surface that are soft, tacky and/or have complex topographies, may be patterned in a simple manner.

The method includes providing a template substrate having a patterned surface inked with a composition of interest. The template substrate, herein referred to as a mold or as a stamp, may comprise a polymer. Generally, polymers which are used for the stamp in micro-contact printing may be used to form the template substrate. In some embodiments, the polymer is an elastomeric polymer. Examples of polymer that may be used to form the template include, but are not limited to polydimethylsiloxane (PDMS), natural rubber, synthetic rubber, agarose, or mixture thereof. In some embodiments, PDMS is used to form the template substrate.

The template substrate may have a patterned surface. The patterned surface on the template substrate may be formed using any suitable patterning methods, such as molding, carving, lithography, etching, and nanoimprinting. In various embodiments, when the template substrate is formed from a polymer, the step of providing a template substrate having a patterned surface comprises (1) generating a polymer stamp with a patterned surface by (i) providing a master template having a patterned surface, (ii) contacting the master template with a solution of a polymer precursor, (iii) curing the polymer precursor solution and (iv) removing the polymer stamp from the master template; and (2) inking the polymer stamp with the composition of interest. For example, a polymer precursor solution may be deposited on or contacted with a master template. Typically, a master template is formed of a material that is sufficiently rigid to allow deposition of the polymer precursor solution, such as a metal or silicon. The polymer precursor solution may be cured or polymerized on the master template, with subsequent separation from the master template, for example by peeling, to form a polymeric template substrate. Accordingly, the polymeric template substrate may assume a pattern negative to the pattern that is present on the master template. For example, the polymeric template substrate may have a negative pattern to the positive pattern on the master template, where the terms "positive pattern" and "negative pattern" indicate that the patterns are the inverse of one another.

The template substrate has a composition of interest inked thereon. The term "inked" as used herein refers to deposition of the composition of interest on a substrate. The composition of interest may be an aqueous solution or a dispersion or colloid, such as a suspension or emulsion. In various embodiments, the composition may include a biomolecule species. As used herein, the term "biomolecule species" refers to any molecule that may be of biological origin and/or interact with a cell that is in contact with it. For example, the biomolecule species may include, but are not limited to, peptides, polypeptides, proteins, oligonucleotides, polynucleotides, carbohydrates, lipids, small molecules, and haptens. In various embodiments, the biomolecule species is fibronectin or collagen. The composition may be formed on the template substrate using any suitable deposition method, such as dip coating, spray coating, painting, sputtering, self assembly or by immersing the template in a solution containing the composition. Subsequent to inking the inked template substrate may be subjected to one or more drying steps.

The method of the present invention further comprises contacting the patterned surface of the template substrate with an intermediate substrate. In so doing, the composition that is inked on the template substrate is transferred to the surface of the intermediate substrate. The composition that is inked on the template substrate may be in a liquid form when brought into contact with the intermediate substrate. In various embodiments, the composition that is inked on the template substrate is dried prior to contact with the intermediate substrate. For example, the composition may be blown dry using a dryer. Even though the composition may also be left to dry naturally, it is generally preferred to blow dry the composition as it allows formation of a more uniform monolayer on the template substrate. The intermediate substrate may be a polymer film. In various embodiments, the polymer of the polymer film used to form the intermediate substrate is a water-soluble polymer. Examples of water soluble polymers that can be used include, but are not limited to, polyvinyl alcohol and polyethylene glycol. In one embodiment, the intermediate substrate comprises polyvinyl alcohol.

Generally, the intermediate substrate has a thickness that is sufficient to allow handling of the substrate, while at the same time, having a thickness that is low enough for ease of dissolution of the intermediate substrate in a subsequent step. In various embodiments, the intermediate substrate may be in the form of a thin film. The intermediate substrate may have a thickness of about 10 μm to about 200 μm, such as about 10 μm to about 100 μm, or about 10 μm to about 50 μm. In some embodiments, the intermediate substrate has a thickness of about 44 μm.

The patterned surface of the template substrate that is inked with the composition of interest may be contacted with the intermediate substrate for a time period that is sufficient to transfer the composition from the template substrate to the intermediate substrate. The time period required may depend on the composition of interest, the type of template substrate, the size of the pattern on the template substrate and the type of intermediate substrate used. For example, the amount of contact time required may depend on the ease at which the composition of interest, such as protein or DNA, can be transferred. In case the composition of interest is protein, the contact time required may also vary between different types of protein. For example, it has been found that fibronectin is easier to be transferred compared to collagen, thereby resulting in a shorter contact time requirement. In some embodiments, the contact time period to transfer fibronectin from the template substrate to the intermediate substrate is 1 minute. The amount of contact time required may also depend on the absorption ability of the composition of interest by the substrate. For example, it has been found that transfer printing using various embodiments of the invention on the 2.1 kPA PDMS substrate is easier than that carried out on the 2.6 kPa polyacrylamide gel substrate, since PDMS is sticky and therefore absorbs protein relatively easily. Generally, the time period required may range from about 1 minute to about 60 minutes, such as about 20 minutes or about 30 minutes.

In some embodiments, the template substrate is placed on the intermediate substrate with application of an external pressure force to the template substrate to hold the template substrate in place and/or to facilitate transfer of the composition to the intermediate substrate. The pressure force exerted on the template substrate may be sufficiently low such that the intermediate substrate is not imprinted or does not deform. In some illustrated embodiments, for example, a 50 g rod weight is placed on the template (see, Example 3). In other embodiments, the template substrate is placed on the intermediate substrate without application of an external pressure force to the template substrate.

The method according to the present invention further comprises removing the template from the intermediate substrate. The surface of the intermediate substrate comprising the composition is then contacted with the substrate. In various embodiments, the surface of the intermediate substrate is placed in conformal contact with the substrate. The intermediate substrate may be contacted with the substrate in such a way that it conforms to the surface topography present on the substrate. In this manner, surfaces having a complex topography such as the curved surface of a cylindrical object or a spherical object may be micropatterned.

In various embodiments, the substrate or the surface of the substrate is soft, tacky or both. As used herein, a "soft" substrate is defined as a substrate comprising a material having a Young's modulus of between about 1 Pa to about 50 kPa, such as about 1 kPa to about 50 kPa, or about 1 kPa to about 25 kPa. In some embodiments, the entire substrate is soft. In some embodiments, only the surface of the substrate is soft. The patterned surface of the substrate may be tacky, i.e. the core of the substrate may or may not be formed from a non-tacky material. The substrate may comprise a material selected from the group consisting of silicone polymers such as polydimethylsiloxane (PDMS), hydrogels such as polyacrylamide gels, and poly(N-isopropylacrylamide), collagen, fibrin, gelatin, and alginate.

The substrate may comprise a tackifier. A "tackifier" refers to a substance added to improve the initial and extended tack range of a material. Examples of tackifier include, but are not limited to, a resin, hydrocarbon, terpene, and alkylphenol.

In some embodiments, the surface of the substrate has a non-planar topography. The non-planar topography may include an arcuate feature, a curved feature or a spherical feature. In various embodiments, the substrate is a sphere, a curved surface of a cylinder or a curved surface of a cone.

The method according to the present invention may include functionalizing the substrate with a compound prior to contacting with the surface of the intermediate substrate comprising the composition of interest, in order to facilitate transfer of the composition to the substrate. The composition may be physically attached or chemically bonded to the substrate. In various embodiments, the composition is chemically bonded to the substrate. For embodiments in which the composition comprises protein and the substrate comprises PDMS, glutaraldehyde may be used. For embodiments in which the composition comprises protein and the substrate comprises polyacrylamide gel, a compound such as N-Sulfosuccinimidyl-6-(4-azido-2-nitrophenylamino) hexanoate or $N_2H_4$ may be used.

The intermediate substrate may be contacted with the substrate for a time period that is sufficient to transfer the composition from the intermediate substrate to the substrate. The time period required may depend on the type of composition, the type of intermediate substrate and the type of substrate used. Generally, the time period required may range from about 1 minute to about 60 minutes, such as about 20 minutes or about 30 minutes.

The method according to the invention comprises removing the intermediate substrate by dissolution using a solvent, solvent mixture or solvent system. The solvent used for dissolving the intermediate substrate may comprise water. Examples of solvent include, but are not limited to, an aqueous solution, a buffer solution such as phosphate buffered saline, and water. In various embodiments, the solvent is a buffer solution. In preferred embodiments of the invention, the solubility of the composition in the solvent is lower than the solubility of the intermediate substrate in the solvent, such that when the solvent is used to dissolve the intermediate substrate, a substantial portion or all of the composition remains on the substrate.

In a second aspect, the invention provides a patterned substrate made by or obtained by a method according to the first aspect. The patterned substrate formed thereof may be used in tissue engineering. Besides a planar configuration, the patterned substrate formed using a method of the present invention may also have a shape or configuration that more closely mimics tissue complexity, and which is more clinically relevant. In various embodiments, the patterned substrate may be used for making three dimensional scaffolds. The invention also relates to a biosensor comprising a patterned substrate according to the second aspect.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

FIG. 1 is a schematic diagram of a general procedure according to various embodiments of the invention to fabricate a template substrate, and subsequent inking of the template substrate with a composition of interest. In the embodiment shown in the figure, the template substrate comprises a polymer. As shown in FIG. 1A, a liquid pre-polymer 104 is poured on a master template 102. The master template may be formed from silicon. In FIG. 1B, the pre-polymer solution 104 is cured to form a polymer stamp 106 on the master template 102. FIG. 1C shows the structure of the polymer stamp 106 after it has been removed from the master template 102. As can be seen, the polymer stamp 106 has a pattern negative to that of the master template 102. In FIG. 1D, a composition of interest 108 is inked on the polymer stamp 106.

Figure 2:
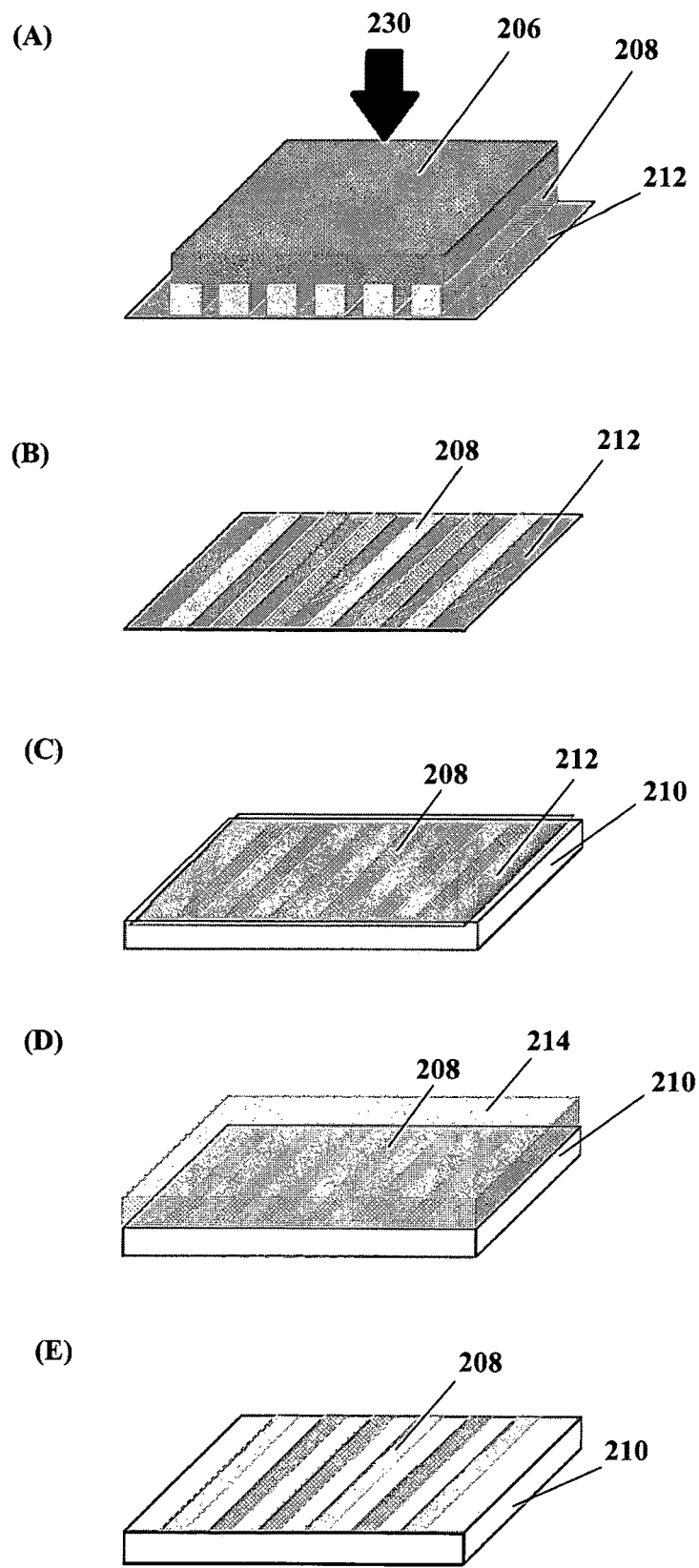
FIG. 2 is a schematic diagram of a micropatterning process according to various embodiments of the invention.

FIG. 2 is a schematic diagram of a micropatterning process according to various embodiments of the invention. In FIG. 2A, a polymer stamp 206 inked with a composition of interest 208 is contacted with an intermediate substrate 212 such as PVA, thereby transferring the composition 208 to the surface of the intermediate substrate 212 as shown in FIG. 2B. A pressure force 230 may optionally be applied to the template substrate. In FIG. 2C, the surface of the intermediate substrate 212 comprising the composition is contacted with a surface of a substrate 210 to transfer the composition 208 to the substrate 210. In FIG. 2D, the intermediate substrate 212 is dissolved with a solvent 214, leaving behind the composition 208 on the substrate 210 as shown in FIG. 2E.

Figure 3:
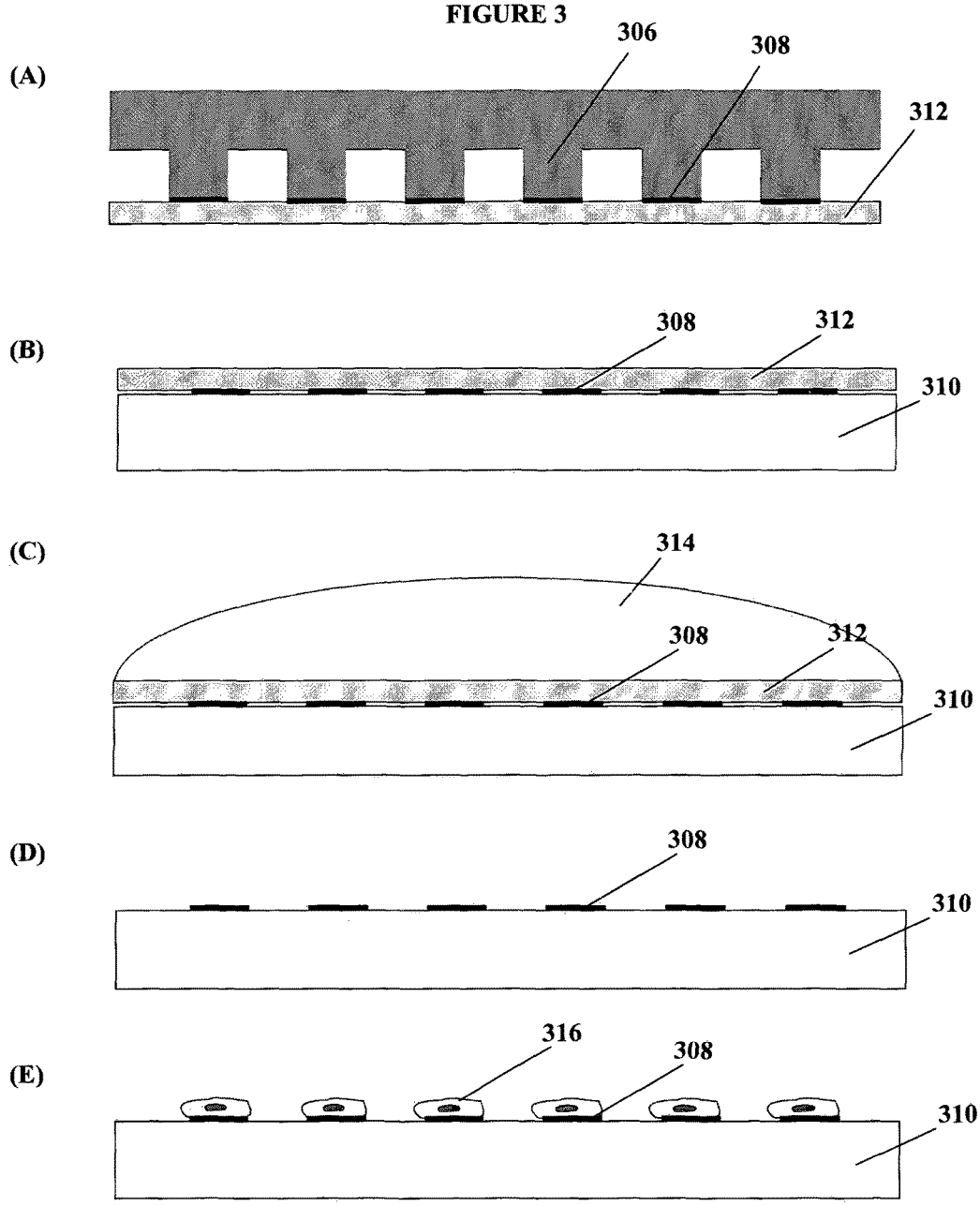
FIG. 3 is a schematic diagram of a micropatterning process according to various embodiments of the invention.

FIG. 3 is a schematic diagram of a micropatterning process according to various embodiments of the invention. In FIG. 3A, a polymeric stamp inked with a composition is contacted with an intermediate substrate, thereby transferring the composition to the intermediate substrate. In FIG. 3B, the side of the intermediate substrate comprising the composition is contacted with a substrate to transfer the composition to the substrate. In FIG. 3C, the intermediate substrate is dissolved using a suitable solvent, leaving behind the composition which is present as a patterned form on the substrate as shown in FIG. 3D. By dissolving the intermediate substrate with a solvent, peeling off of the polymeric stamp after patterning is avoided thereby preventing adherence of the stamp to the substrate. In the embodiment shown in the figure, the composition of interest may be protein. In FIG. 3E, cells are seeded on the patterned protein.

FIG. 4 is a schematic diagram of a conventional microcontact printing procedure. As shown in FIG. 4A, a polymeric mold 406 inked with a compound 408 is contacted directly with a substrate 410, under application of pressure 430. In FIG. 4B, the protein 408 on the mold 406 is transferred to the substrate 410.

FIG. 5 is a schematic diagram of a conventional microcontact printing (µCP) process. In FIG. 5A, the compound 508 on the mold 506 is transferred to the substrate 510 by direct contact of the substrate 510 with the polymeric stamp 506. In FIG. 5B, the compound 508 is present as a patterned form on the substrate 510. In embodiments in which the compound 508 is a protein, cells 516 may be seeded on the compound 508.

Example 1: Polyvinyl Alcohol (PVA) Film Preparation, Substrates Preparation and Characterization Example 1.1: PVA Film Preparation 5 wt % polyvinyl alcohol (PVA) (Sigma P8136) was slowly poured in deionized (DI) water and left at room temperature overnight, followed by magnetic stirring at 90° C. for 2 hours to 3 hours to dissolve the PVA particles. The resulting PVA solution (20 mL) was filtered by a qualitative filter paper (Advantec MFS) and poured into glass petri-dish (150 mm in diameter), and was dried at room temperature in a laminar flow hood overnight for about 24 hours with lid half open to form the film.

The dried PVA film was removed from the petri-dish with a tweezer and paper cutter. The PVA film was cut into round shape with specified diameter of about 2 cm by a SCHMIDT® Presses (SCHMIDT Technology, Germany). The thickness of the film h was determined as:

$$h = \frac{m}{\rho A}$$ Equation (I)

where m is the mass of PVA used, ρ is the density of PVA (1.29 g mL$^{-1}$ according to manufacturer's data), and A is the area of the petri dish. The thickness of the PVA film was about 44 µm in the study.

Example 1.2: Polydimethylsiloxane (PDMS) Substrate and Polyacrylamide (PA) Gel Substrate Preparation To prepare substrates of different stiffness, polydimethylsiloxane (PDMS) (Sylgard 184, Dow Corning) with three types of cross-link ratio (cross linker:base ratio of 1:10, 1:50 and 1:70) were used. The pre-polymer solutions were poured into a 6-well cell culture plate, and the plates were baked in an oven at 65° C. for 24 hours.

Soft polyacrylamide (PA) gels were prepared according to the procedure previously reported in Tse J R et al. (Tse J R et al., 2010, *Current Protocols in Cell Biology*, 10:1-10.6). 4% acrylamide was mixed with 0.15% bis-acrylamide to make 2.6 kPa PA gel.

All the plates and films were ultra-violet (UV) sterilized before use. Before patterning, to improve protein attachment on bio-inert surface, 308 kPa PDMS and PA gel substrates were treated with 0.2 mg mL$^{-1}$ N-Sulfosuccinimidyl-6-(4'-azido-2'-nitrophenylamino) hexanoate (Sulfo-SANPAH, Pierce Biotechnology) in 50 mM (4-(2-hydroxyethyl)-1-piperazineethanesulfonic acid) (HEPES buffer) (PAA laboratories) under 365 nm UV lamp (VL-215 LC; Vilber Lourmat) for 10 minutes according to the methods described previously in Tse J R et al. Afterwards, samples were dried in 60° C. oven for 30 minutes.

To prepare the substrate with curved surface, the 1:10 PDMS pre-polymer solution was poured into the curvature of a disposable dropper and cured. Subsequently, the outer curvature of the dropper was peeled off and the cross-linked PDMS was cut into specified dimensions. To measure the shear modulus of PDMS, different cross linking ratio of PDMS prepolymer solution was poured into a mold which gives a round PDMS sheet with a thickness of about 1 cm after cross linking.

Example 1.3: Characterization of Substrate

The shear elastic modulus (G') of the PDMS sheet was measured by a Physica Rheometer (Anton Paar) and was converted to Young's modulus (E') using the equation $$E' \approx 3G'$$ Equation (II)

Example 2: PDMS Stamp Fabrication and Inking

With reference to the general procedure shown in FIG. 1, silicon master templates bearing various topographic features were fabricated by standard photolithography and etching method. Subsequently, the silicon master templates were cleaned with Piranha solution and DI water, followed by treatment with octadecyltrichlorosilane (OTS) (Sigma). PDMS stamps were fabricated by casting the 1:10 PDMS solution against the silicon master templates as previously described in Tay C Y et al. (Tay C Y et al., 2010, *Exp Cell Res*, 316:1159-68). Briefly, the 1:10 PDMS solution was poured over the master, left in vacuum oven for degassing, and transferred for curing at 100° C. for 2 hours. Afterwards, the PDMS layers were gently peeled off by hand, and designed patterns were generated on the PDMS surface. The PDMS stamps were washed in ethanol in an ultrasonic cleaner bath for 15 minutes to remove particles before use.

Figure 9:
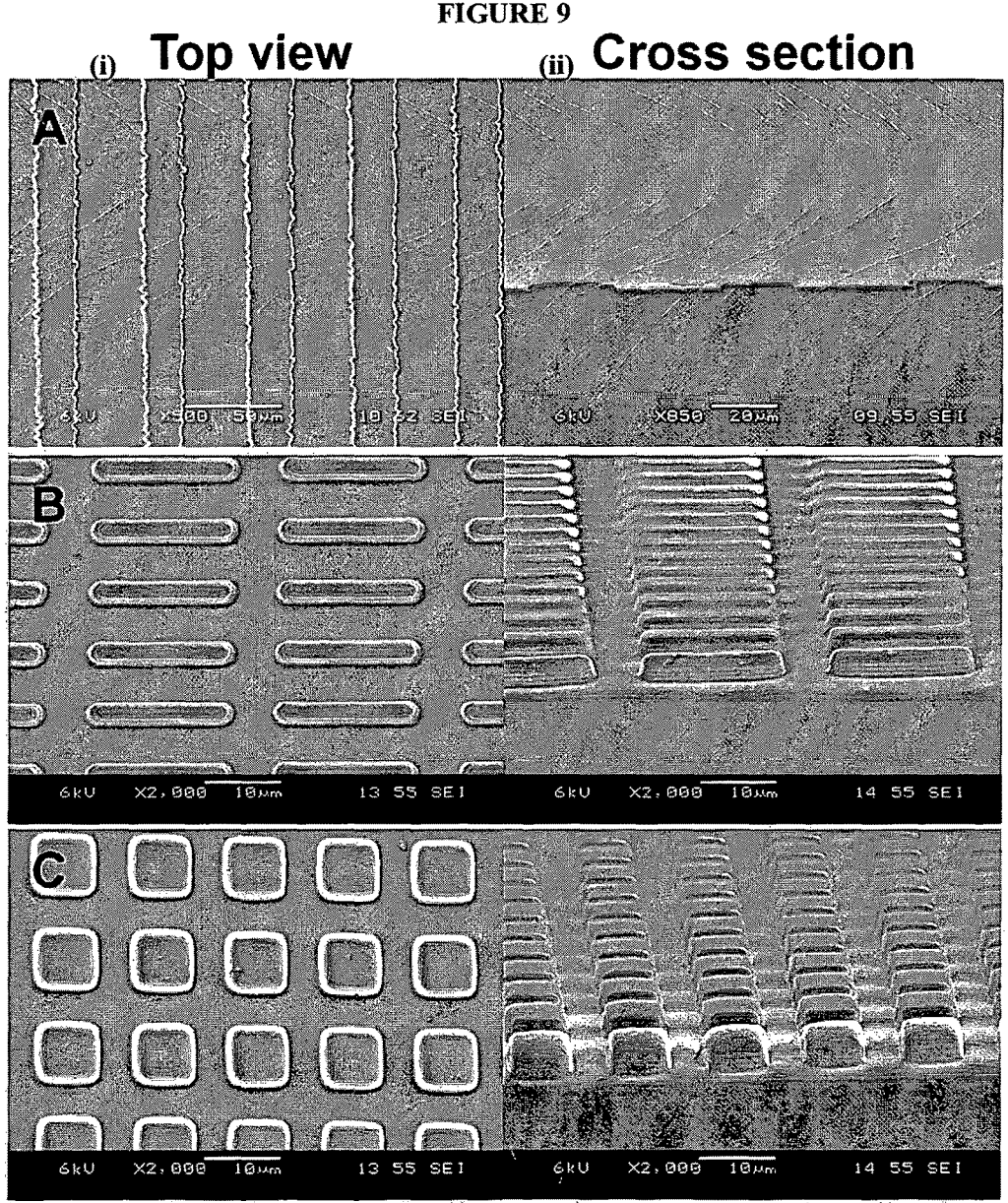
FIG. 9 are Scanning Electron Microscope (SEM) images showing the topographies on polydimethylsiloxane (PDMS) stamps, with images on the (i) left column showing the top view, and (ii) right column showing a perspective view.

FIG. 9 are Scanning Electron Microscope (SEM) images showing the topographies on polydimethylsiloxane (PDMS) stamps, with images on the (i) left column showing the top view, and (ii) right column showing a perspective view. FIG. 9A depicts a strip shape pattern, with each pattern having a dimension of about 40 µm in length, 20 µm in width, and 1 µm in height. FIG. 9B depicts a rectangular shape pattern, with each pattern having a dimension of about 20 µm in length, 2.5 µm in width and 5 µm in height. FIG. 9C depicts a square shape pattern, with each pattern having a dimension of about 5 µm in length, 5 µm in width and 5 µm in height.

For inking, the PDMS stamp was immersed with human fibronectin (FN) (BD Biosciences) in PBS (50 µg mL$^{-1}$) or collagen type I from rat tail (COLI) (Invitrogen) diluted in PBS (50 μg mL$^{-1}$) in a cell culture hood for 1 hour, followed by blow drying with pressurized purified nitrogen gas.

Example 3: Microcontact Printing

With reference to FIG. 4 which shows a general procedure for a conventional micro-contact printing process, the inked stamp was placed in conformal contact with PDMS substrates for 20 min with a 50 g rod weight on it. Afterwards, the stamp was gently peeled off from the substrates followed by washing with phosphate buffered saline (PBS) three times.

Novel μCP method according to an embodiment of the invention was carried out with reference to the general procedure shown in FIG. 5. The inked PDMS stamp was placed onto the freshly-made PVA film for 20 min in a cell culture hood with a 50 g rod weight on it. Then the patterned side of the film was placed in conformal contact with soft and/or tacky target substrate and was left in a laminar flow hood for 30 min. After incubation, PBS was applied to rinse the substrate three times (5 min each time) to dissolve and wash away the PVA film completely. The non-printed region of both conventional and novel μCP groups was then passivated with 1 wt % Pluronic F-127 (BASF) for 1 hour at 37° C. followed by washing with PBS three times.

Example 4: hMSCs Culture and Seeding

Cryopreserved hMSCs (Cambrex) were cultured as previously described in Yu H et al. (Yu H et al., 2010, Biochem Biophys Res Co., 393:150-5). When conducting the experiments, hMSCs were harvested and plated at a density of $3 \times 10^3$ cells cm$^{-2}$ in a Dulbecco's modified Eagle's medium (DMEM) low glucose culture medium without serum and incubated for 1 hour. After cells attached to the patterned proteins, complete medium with supplement of 10% fetal bovine serum (FBS) and 1% antibiotics was applied to remove non-attached cells. Phase contrast images were captured with an inverted microscope (Eclipse TS 100, Nikon) at 48 hours, and 7 days to check the cell morphology.

Example 5: Immunofluorescence Imaging and Analysis

Briefly, cells were fixed at 48 hours after seeding with 4% paraformaldehyde for 10 min and then permeabilized with 0.1% Triton X-100 for 5 min and followed by blocking with 5% bovine serum albumin (BSA) for 1 hour. The primary antibodies were mouse anti-collagen type I (1:400), or rabbit anti fibronectin (1:400) (CHEMICON) which incubated with the samples at 37° C. for 1 hour, and secondary antibodies were Alex Fluor 488 goat anti-mouse IgG (1:400), or chicken anti-rabbit IgG (1:400) (Invitrogen), and TRITC-conjugated Phalloidin (1:400) (CHEMICAON) which was applied at room temperature for 1 hour. 4',6-diamidino-2-phenylindole (DAPI) (1:1000) (CHEMICON) was applied for 10 minutes to stain cell nuclei. Fluorescence images were captured using an upright fluorescent microscope (Eclipse 80i, Nikon).

Example 6: Cell Alignment Analysis and Surface Topographies Construct

Cell alignment was analyzed quantitatively by the angle measurement function using ImageJ software. Fluorescence images of the cylinder with curved surface were captured using an inverted confocal microscope system (TCS SP5, Leica). The 3D reconstructions of the patterned surface were computed using average 3D projection function of Leica Application Suite software.

Example 7: Statistical Study

All assays were repeated three times for each experimental group and were expressed as means±standard deviation (SD).

Example 8: Advantages of Trans-Printing Over Conventional Microcontact Printing on Flat Substrates As discussed in the background section, conventional micro-printing processes suffer from draw-backs, in particular for soft, tacky and/or surfaces having a complex topography, such as stamp adhering to the tacky substrates and causing distortion in patterns.

Figure 6:
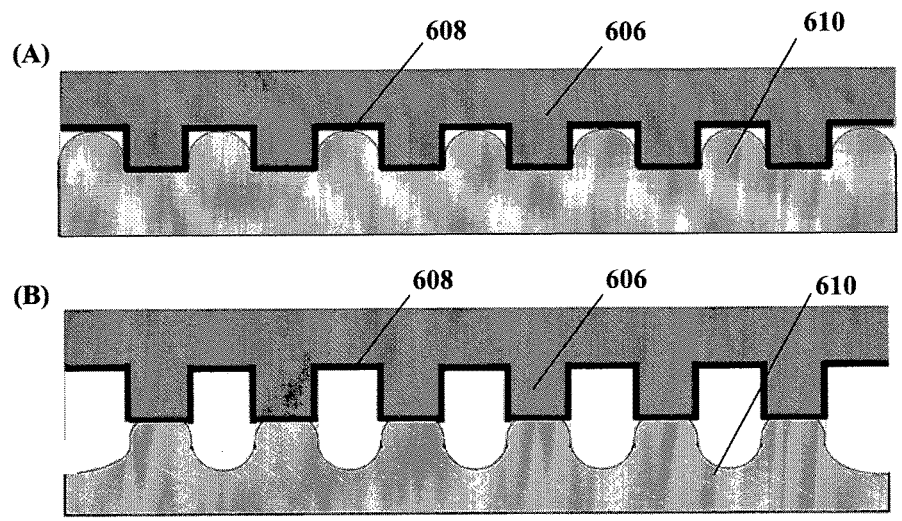
FIG. 6 is a schematic diagram illustrating the limitations of conventional micro-contact printing on soft and/or tacky substrates.

FIG. 6 is a schematic diagram illustrating the limitations of conventional micro-contact printing on soft and/or tacky substrates. FIG. 6A shows a stamp 606 comprising a composition 608 in direct contact with a soft substrate 610. As depicted in the figure, contact of the stamp 606 with the soft substrate 610 may result in sagging of the substrate 610, in particular, when excessive pressure force is applied to the stamp 606. FIG. 6B depicts the stamp 606 adhering to a tacky substrate 610 when removing the stamp 606 from the substrate surface after printing. In both cases, the patterned composition on the substrate is distorted.

Figure 7:
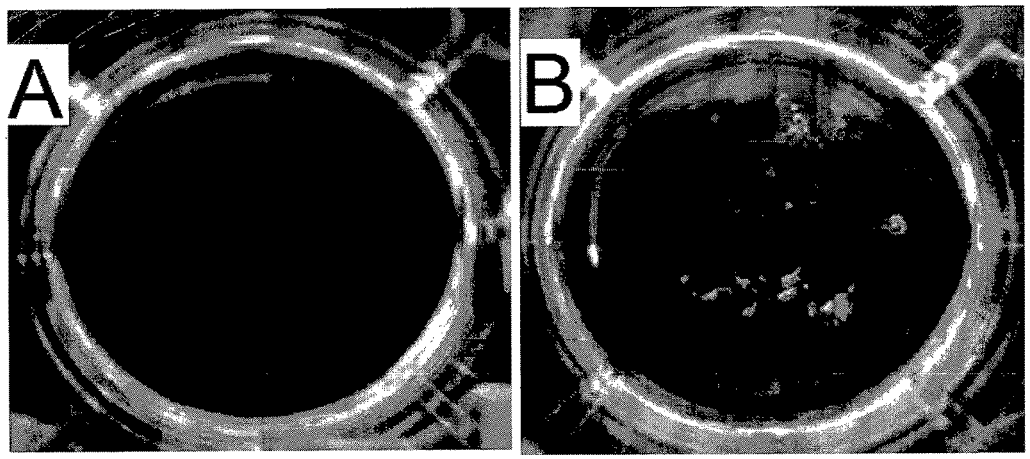
FIG. 7 are fluorescence images of a tacky substrate (A) before patterning and (B) after patterning. From the images, white patches can be seen in FIG. 7B, demonstrating that the tacky surface was damaged after patterning.

FIG. 7 are fluorescence images of a tacky substrate (A) before patterning and (B) after patterning. From the images, white patches can be seen in FIG. 7B, demonstrating that the tacky surface was damaged after patterning.

Figure 8:
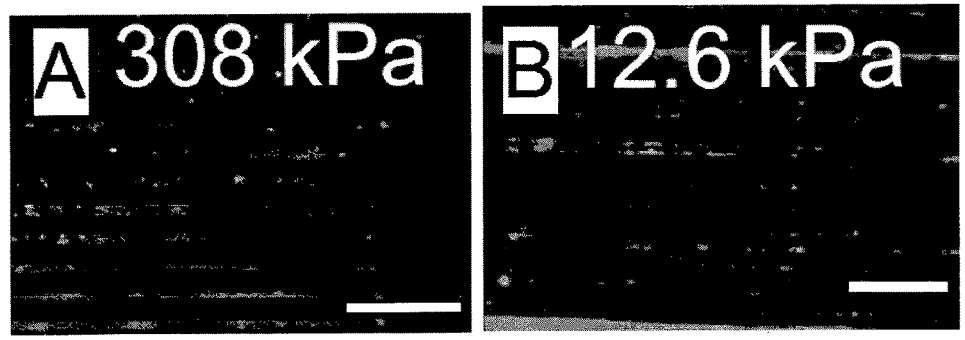
FIG. 8 are immunostaining fluorescence images of conventional micro-contact printing of fibronectin (FN) on different substrates having a Young's modulus of (A) 308 kPa; (B) 12.6 kPa, and (C) 2.1 kPa. As can be seen from the images, conventional micro-contact printing suffers from limitations that the polymeric stamp adheres to soft and/or tacky substrates which disrupt the patterns (see FIGS. 8B and 8C). The scale bar in the figures denotes a length of 100 μM.
Figure 8:
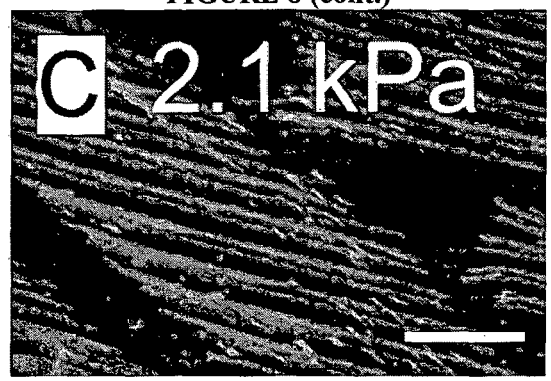

FIG. 8 are immunostaining fluorescence images of conventional micro-contact printing of fibronectin (FN) on different substrates having a Young's modulus of (A) 308 kPa; (B) 12.6 kPa, and (C) 2.1 kPa. As can be seen from the images, conventional micro-contact printing suffers from limitations that the polymeric stamp adheres to soft and/or tacky substrates which disrupt the patterns (see FIGS. 8B and 8C). The scale bar in the figures denotes a length of 100 μm.

As the problem mainly occurred during removal of stamp in conventional μCP, the problem may be avoided by preventing the deformation of substrates and subsequent distortion of the patterns by introducing a water soluble trans-printing media, thus omitting the stamp removal step on the soft/tacky substrates. To test this idea, a novel μCP process based on the general procedure in FIG. 2 was performed on 308 kPa, 12.6 kPa, and 2.1 kPa PDMS substrates as well as 1.1 kPa and 2.6 kPa soft PA gel substrates to verify its conformance on hard, soft, and tacky surfaces respectively.

PDMS was chosen as the substrate due to its ease of fabrication, bio-inertness, and non-toxicity. PDMS of various shear moduli and tackiness was prepared by changing the ratio of cross-linker to the base. The ratios used were 1:10, 1:50, and 1:70 which correspond to Young's modulus of 308 kPa, 12.6 kPa, and 2.1 kPa, respectively by using Equation (II). Both the 12.6 kPa and 2.1 kPa soft PDMS have great potential use in soft tissue engineering since they mimic muscle and neuron environment respectively.

In this method, the inked stamp was placed onto the freshly-made PVA film instead of printing directly onto the final target substrate. In this step, the pattern was transferred from the stamp to the PVA film, and the film now functions as a trans-print media. Then the patterned side of the film was placed in conformal contact with soft and/or tacky target substrate. The proteins would bind to the underneath substrates before dissolving the PVA film leaving behind patterns, such as that shown in FIG. 10.

Figure 10:
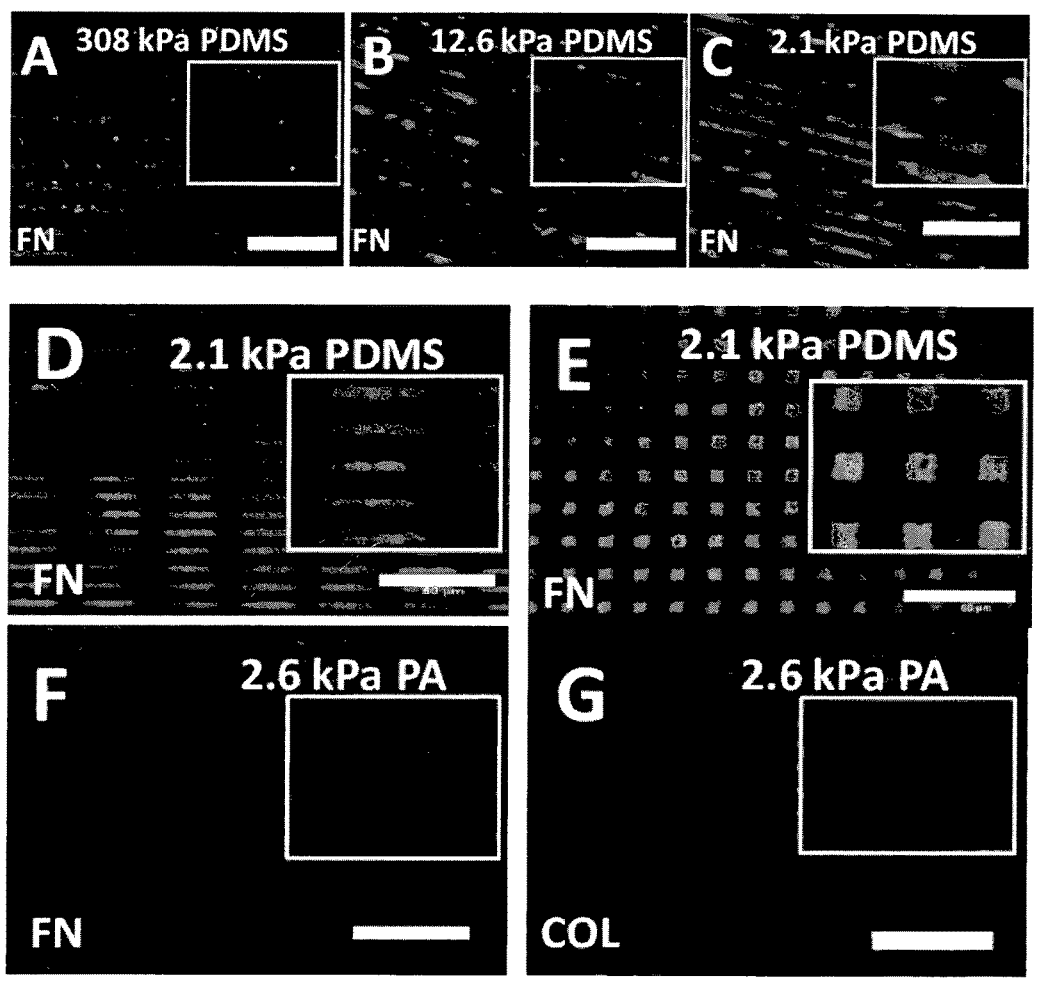
FIG. 10 are immunostaining fluorescence images of fibronectin (FN) and collagen (COL) on different substrates according to various embodiments of the present invention.

FIG. 10 are immunostaining fluorescence images of fibronectin (FN) and collagen (COL) on different substrates according to various embodiments of the present invention. FIGS. 10A to 10 C depicts fibronectin (FN) patterned on a PDMS substrate having a Young's modulus of (A) 308 kPa; (B) 12.6 kPa, and (C) 2.1 kPa. FIG. 10D to 10G depicts fibronectin (FN) (D to F) and collagen (COL) (G) patterned on a PDMS substrate surface having features of different sizes and shapes. The scale bar in FIGS. 10A to 10C denotes a length of 100 μm and the scale bar in FIGS. 10D to 10E denotes a length of 50 μm.

Generally, this additional trans-print step only requires a short duration such as 30 minutes, and PVA is a cheap chemical. More importantly, it can avoid the problems with conventional micro-printing such as that shown in FIGS. 6 to 8. Through the use of the trans-print film, patterns on soft and/or tacky surfaces can be created. Furthermore, the pattern resolution and quality may be improved. The trans-patterned film offers a solvent-free inking stamp which will reduce the diffusion of inking molecules from the remainder of the conventional μCP stamp.

Therefore, the trans-print stamp according to embodiments of the present invention facilitates printing of small isolated features with improved geometric control of the patterns. After incubation, phosphate buffer saline (PBS) was applied to dissolve and wash away the PVA film completely and no stamp removal step was required. PVA was chosen as the trans-print media as it is a water-soluble synthetic polymer with excellent biocompatibility and physical properties and has low cost. It has been widely used as surfactant to disperse particles in drug delivery system and as binding and coating reagents in food industries. However, this technique is not limited to PVA, it is expected that other water soluble materials, such as polyethylene glycol (PEG) can also be employed as the trans-print media.

Immunostaining was done on the printed protein to check the μCP efficiency and shown in FIG. 10. The results show that by using the novel trans-print method, much better patterns on all substrates could be achieved, as compared with the conventional method in FIG. 8A to 8C.

To demonstrate that the novel method was also applicable to different patterns, two other kinds of patterns were used for printing on 2.1 kPa soft PDMS with a dimension of 20 μm×2 μm and 6.3 μm×6.3 μm. FIGS. 10D and 10E showed that efficient pattern transfer and good resolution could be achieved for patterns with dimensions as small as 2 μm to as big as 20 μm on soft and tacky PDMS substrates. The versatility of the technique is shown by printing FN (FIG. 10F) and collagen (FIG. 10G) on 2.6 kPa PA gel. Immunostained fibronectin (FN) and collagen type I (COL) showed that effective pattern was transferred onto 2.6 kPa polyacrylamide (PA) gel. These results indicated that the transferred proteins worked and this novel technique was generic and could be applied to various proteins as inks. It was also demonstrated that this versatile technique can be applied to a wide range of substrates using various inks regardless of their modulus and very importantly at a low cost and is simple as compared to other reported micro or nano patterning methods such as Dip-Pen Lithography or laser scanning lithography. Since the resolution is dependent on the PDMS stamp but not the PVA film, the pattern size may go down to 0.5 μm or smaller with the aid of high resolution PDMS stamp fabricated through a special lithographic molding technique.

Figure 15:
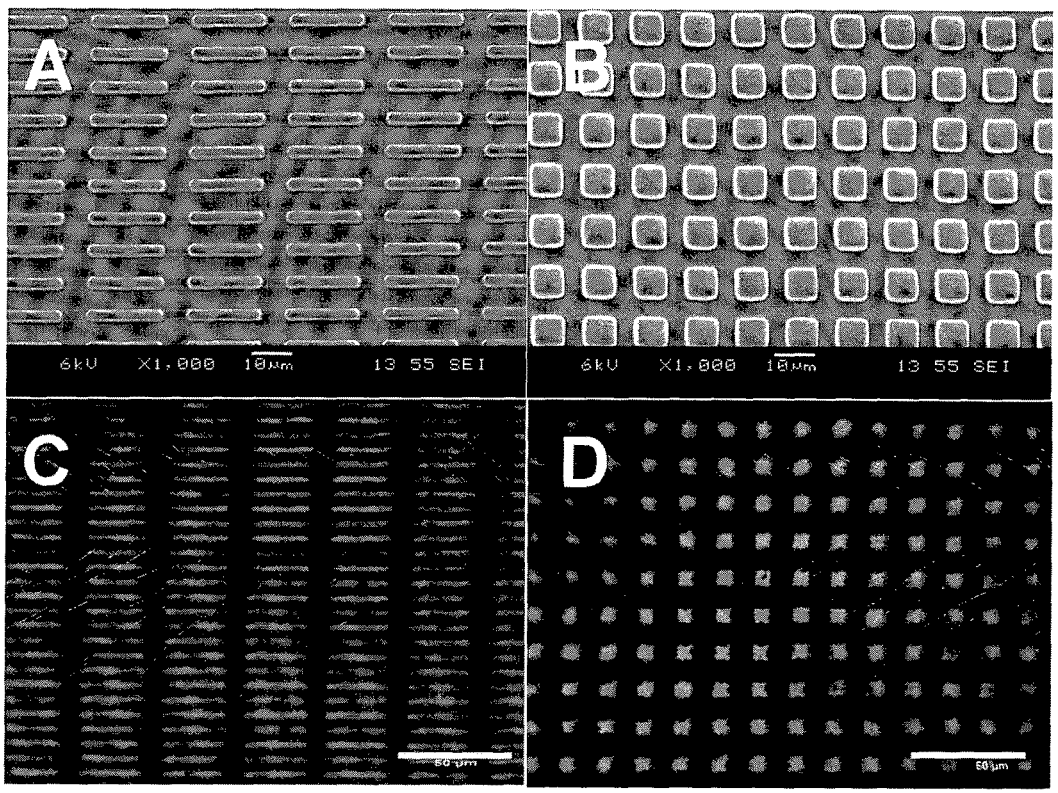
FIG. 15 are SEM images and fluorescent images showing two types of patterns obtained using the trans-print method according to various embodiments of the invention.
Figure 16:
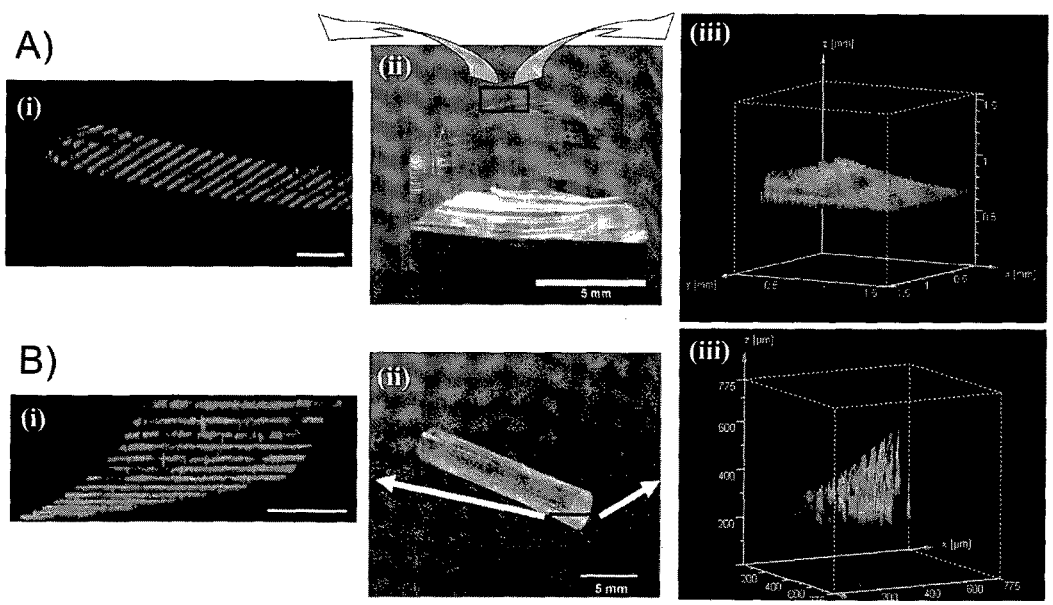
FIG. 16 are optical images demonstrating that the microprinting process according to various embodiments of the invention can be used on curved surfaces. The 3D topological images in A(iii) and B(iii) were produced using Leica Allication Suit software to show the topography of the patterned surface.

Further images are shown in FIG. 15. FIG. 15 are SEM images and fluorescent images showing two types of patterns obtained using the trans-print method according to various embodiments of the invention. FIGS. 15A and 15B are the SEM images of the stamps, while FIGS. 15C and 15D are the patterns created on 1:70 soft and sticky PDMS substrate. The scale bar in the fluorescent images denotes a length of 50 μm.

Example 9: Micropatterned PDMS Induced Cell Alignment

To further confirm the novel μCP efficiency for protein patterning, hMSCs were seeded on 12.6 kPa and 2.1 kPa PDMS substrates patterned with collagen type I (COLI) or fibronectin (FN) by the novel trans-print technique according to embodiments of the present invention.

Figure 11:
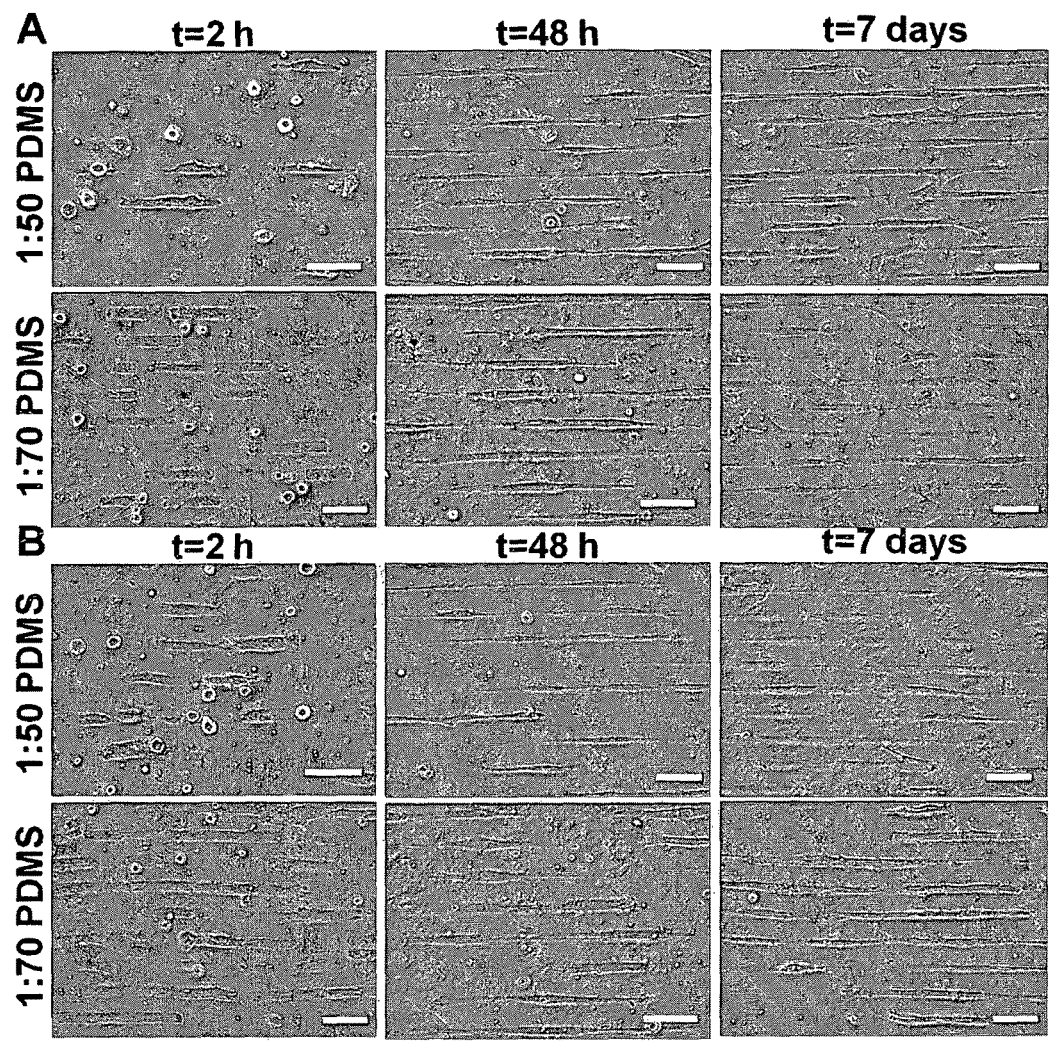
FIG. 11 are optical images showing human mesenchymal stem cells (hMSCs) alignment on 1:50 and 1:70 PDMS substrates (having a Young's modulus of 12.6 kPa and 2.1 kPa respectively) with (A) COL and (B) FN, at time=2 hours, 48 hours and 7 days. The rounded cells in the images taken at time=2 hours are the unpatterned cells which were flowed up. The scale bar denotes a length of 50 μm. The optical images showed good hMSCs alignment with the protein pattern on the substrate.
Figure 12:
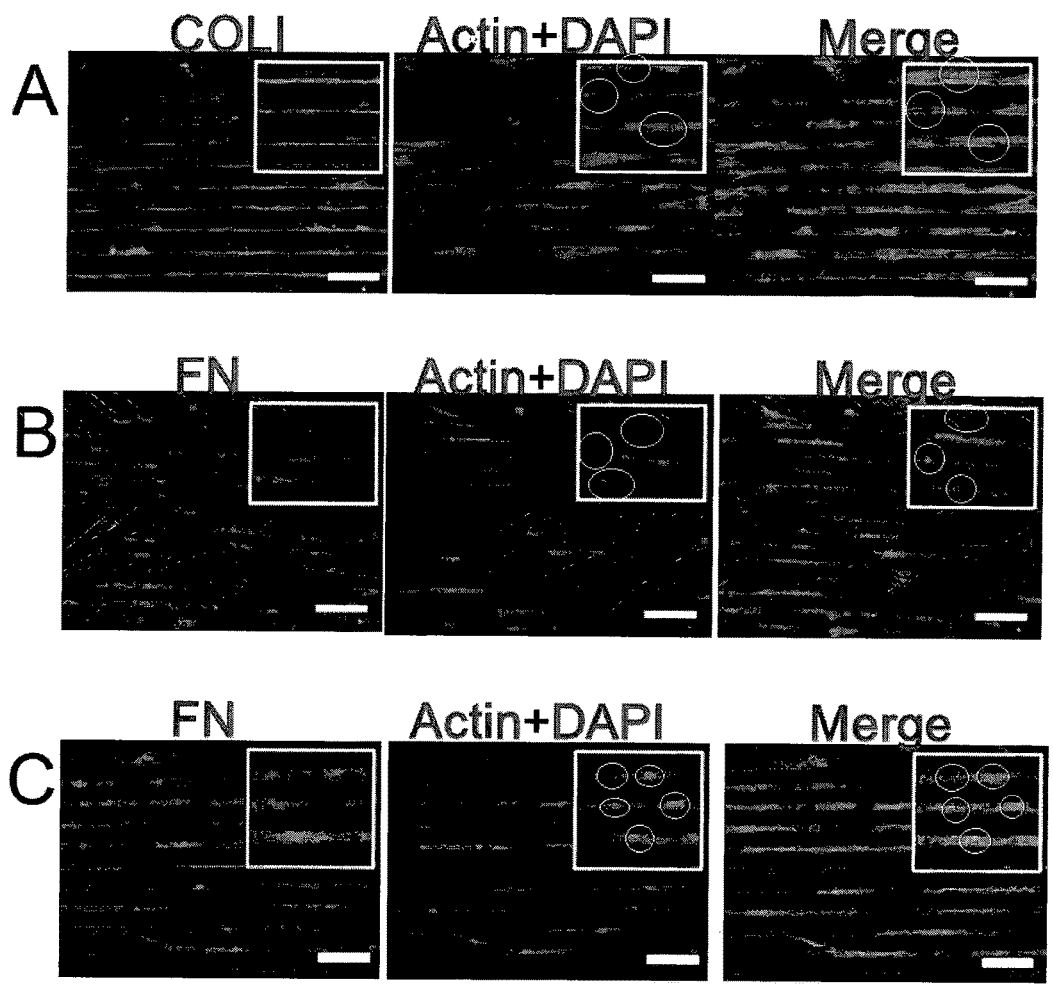
FIG. 12 are fluorescent images of human mesenchymal stem cells (hMSCs) alignment on 2.1 kPa PDMS substrates with (A) COL, and (B) FN. The box shows a magnified view of the enclosed area. The circled portions indicate stained cell nucleus which are stained by 4',6-diamidino-2-phenylindole (DAPI). The lighter areas in the images titled "Actin+DAPI" indicate F-actin staining. (C) Also shown are fluorescent images of human mesenchymal stem cells (hMSCs) alignment on 2.6 kPa PA gel with FN. The images indicate good alignment of the cells on the substrate. The scale bar in the images denotes a length of 50 μm.

FIG. 11 are optical images showing human mesenchymal stem cells (hMSCs) alignment on 1:50 and 1:70 PDMS substrates (having a Young's modulus of 12.6 kPa and 2.1 kPa respectively) with (A) COL and (B) FN, at time=2 hours, 48 hours and 7 days. The rounded cells in the images taken at time=2 hours are the unpatterned cells which were flowed up. The scale bar denotes a length of 50 μm. The optical images showed good hMSCs alignment with the protein pattern on the substrate. FIG. 12 are fluorescent images of human mesenchymal stem cells (hMSCs) alignment on PDMS substrates with (A) COL, and (B) FN. The box shows a magnified view of the enclosed area. The circled portions indicate stained cell nucleus which are stained by 4',6-diamidino-2-phenylindole (DAPI). The lighter areas in the images titled "Actin+DAPI" indicate F-actin staining. (C) Also shown are fluorescent images of human mesenchymal stem cells (hMSCs) alignment on 2.6 kPa PA gel with FN. The images indicate good alignment of the cells on the substrate. The scale bar in the images denotes a length of 50 μm.

Referring to FIGS. 11 and 12, both optical and fluorescent images showed hMSCs exhibited good alignment on 12.6 kPa and 2.1 kPa PDMS substrates during the experimental period of 7 days on COLI (FIG. 11A and FIG. 12A) and FN (FIGS. 11B and 12B) respectively. Besides PDMS, the PVA trans-printing method was also applied on 2.6 kPa PA gel, and hMSCs showed good alignment as well, as shown in FIG. 12C.

Figure 13:
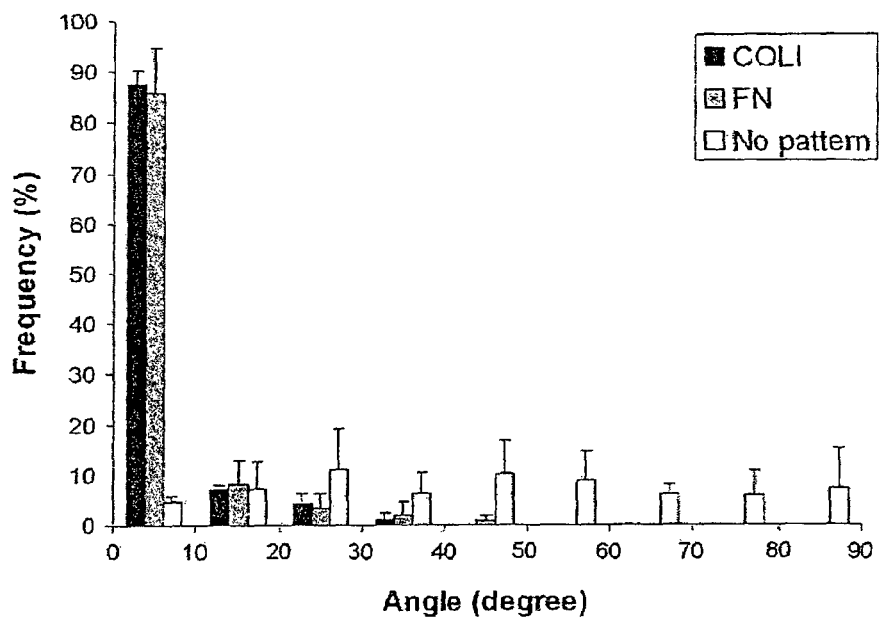
FIG. 13 is a graph showing the statistical result on distribution of hMSCs on 2.1 kPa PDMS (n=80). From the graph, it can be seen that most of the hMSCs were oriented within 10° and 20° of the angle on the substrates patterned with COL or FN using the trans-print method according to various embodiments of the invention. Otherwise, on 1:70 PDMS coated with a homogeneous layer of FN without pattern, hMSCs were randomly distributed at all angles.

FIG. 13 is a graph showing the statistical result on distribution of hMSCs on 2.1 kPa PDMS (n=80). From the graph, it can be seen that more than 85% of the hMSCs were oriented within 10° and 20° of the angle on the 2.1 kPa PDMS patterned with COLI or FN using the trans-print method according to various embodiments of the invention. Otherwise, on 1:70 PDMS coated with a homogeneous layer of FN without pattern, hMSCs were randomly distributed at all angles. The patterned proteins were viable leading to cell attachment and then alignment along the pattern direction, demonstrating that this novel trans-print method is mild and could produce excellent micropatterning efficiency.

The ink transfer efficiency of this method, as measured using fluorescent intensity, reached a remarkable 87% of protein intensity compared to that using conventional μCP (calculated by fluorescent intensity between conventionally patterned FN on 308 kPa PDMS and PVA patterned FN on 308 kPa PDMS, using ImageJ) when performed on 12.6 kPa hard PDMS, showing that the "photocopy" process was efficient and was not affected when PVA film was washed away. This demonstrated high patterning efficiency and this small loss could optionally be addressed by increasing the ink initial concentration.

Example 10: Advantages of Trans-Printing μCP Applied to Curved Surface

Recently, 3D micropatterning has attracted enormous attention because of the increasing demand to mimic tissue complexity and develop clinically relevant tissues. Several techniques have been developed for that purpose, such as conventional photolithographic patterning, electrochemical deposition, laser cutting, and soft-lithographic approaches. These techniques, again, are either complex or require tedious optimization and specific equipment for operation. Research have been carried out in which patterning of palladium colloids was done on a glass bottle by rolling the curved surface on inked stamp. However, this method requires the curved substrate to be regular or the stamp would not have conformal contact with the substrate during rolling. Therefore, studies to 3D scaffolds have been extended but with the advantage of being simple and cost-effective and versatile enough to be applied to curved as well as wavy surfaces. To demonstrate the feasibility of this technique in macro scale 3D patterning, a cylindrical model with a diameter of 2 mm was used.

Figure 14:
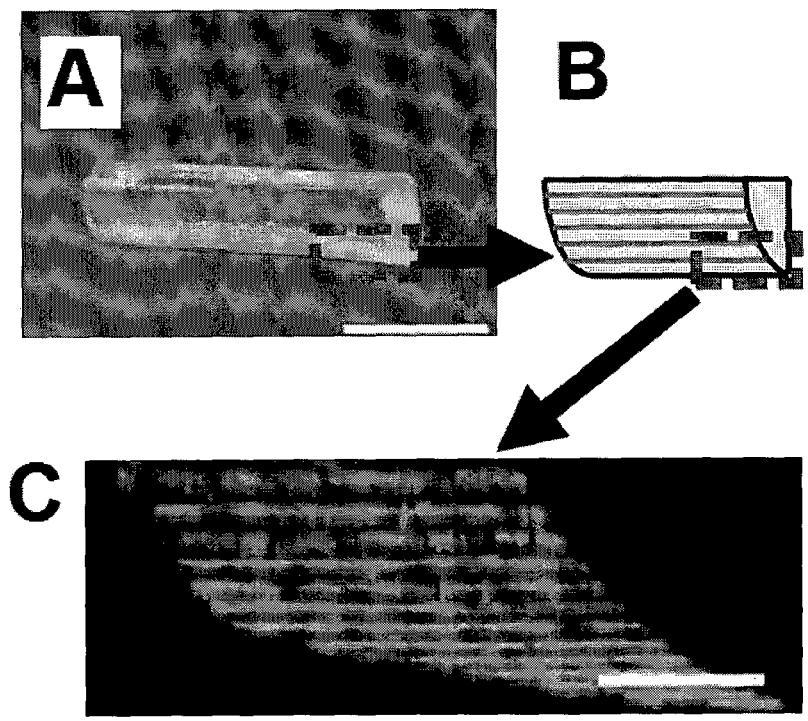
FIG. 14 is (A) an optical image showing a cylinder made from PDMS; (B) a schematic chart of the patterned FN and the scanned section by confocal microscope, and (C) immunostained FN on curved surface of the cylinder. The scale bar in (A) denotes a length of 4 mm, and the scale bar in (C) denotes a length of 50 μm.

FIG. 14 is (A) an optical image showing the cylinder used, wherein the cylinder is made from PDMS; (B) a schematic chart of the patterned FN and the scanned section by confocal microscope, and (C) immunostained FN on curved surface of the cylinder. The scale bar in (A) denotes a length of 4 mm, and the scale bar in (C) denotes a length of 50 μm. Referring to the figure, a strip pattern was created on the cylinder (FIG. 14A) and 2D view graph in FIG. 14B showed the well patterned FN on the curved surface. It is believed that the technique would work on a wavy surface, since PVA film is highly flexible and could easily conform to the shape and contours of irregular substrates. Thus, where conventional μCP is limited to flat surfaces, the transprinting method enables easy patterning on curved surfaces.

In summary, a novel μCP technique to create micropatterns on soft and/or tacky substrates and extended its usage on complex surfaces such as cylinder by means of water-soluble transprint media has been developed. Results have shown that this novel method could create desirable patterns and obtain much better pattern efficiency than the conventional μCP method when applied on soft and tacky PDMS or extremely soft PA gel (2.6 kPa). The versatility of this technique was demonstrated by patterning on different substrates using different proteins as inks. COL and FN, two of the most commonly used extracellular matrix (ECM) proteins were tested. This novel technique may be extended to other proteins and nucleic acids such as DNA, and may also have further potential in chemical patterning and microelectric fabrication. The method according to various embodiments of the invention can create micropatterns on complex or 3D surfaces, such as that demonstrated herein on a small cylinder. As the soft nature is ubiquitous to most biomaterials in soft tissue engineering and some may be as tacky as PDMS, the novel μCP method may be applicable to most cell-materials interaction and other biological studies that involve soft tissues. It is anticipated that this novel μCP technique has a great potential in soft tissue engineering and regenerative medicine.

The invention claimed is:

1. A method of micropatterning a substrate, the method comprising:
    a) providing a mold having a patterned surface inked with a composition of interest;
    b) contacting the patterned surface with a surface of an intermediate substrate, thereby transferring the composition of interest to the surface of the intermediate substrate, whereby the surface of the intermediate substrate is not imprinted;
    c) contacting the surface of the intermediate substrate comprising the composition of interest with a surface of the substrate, thereby transferring the composition of interest from the intermediate substrate to the substrate, wherein the substrate comprises one selected from the group consisting of silicone polymers, polydimethysiloxane, hydrogels, polyacrylamide gels, poly(N-isopropylacrylamide), fibrin, and alginate; and
    d) dissolving the intermediate substrate using a solvent; wherein the composition of interest remains on the substrate after the intermediate substrate is removed.

2. The method of claim 1, wherein the mold comprises a polymer selected from the group consisting of silicone polymers, polydimethylsiloxane, natural rubber, synthetic rubber, agarose and mixture thereof.

3. The method of claim 1, wherein the step of providing a mold having a patterned surface inked with a composition of interest comprises (1) generating a polymer stamp with a patterned surface by (i) providing a master template having a patterned surface, (ii) contacting the master template with a solution of a polymer precursor, (iii) curing the polymer precursor solution, and (iv) removing the polymer stamp from the master template; and (2) inking the polymer stamp with the composition of interest.

4. The method of claim 1, wherein the composition of interest comprises a biomolecule species.

5. The method of claim 4, wherein the biomolecule species comprises one selected from the group consisting of peptides, polypeptides, proteins, oligonucleotides, polynucleotides, nucleic acids, carbohydrates, lipids and haptens.

6. The method of claim 4, wherein the biomolecule species comprises fibronectin or collagen.

7. The method of claim 1, wherein the intermediate substrate is a polymer film.

8. The method of claim 7, wherein the polymer of the polymer film is a water-soluble polymer.

9. The method of claim 8, wherein the water-soluble polymer is polyvinyl alcohol or polyethylene glycol.

10. The method of claim 7, wherein the intermediate substrate comprises polyvinyl alcohol.

11. The method of claim 1, wherein the substrate or the surface of the substrate being contacted with the surface of the intermediate substrate comprising the composition of interest is soft in that it has a Young's modulus of between about 1 Pa to about 50 kPa, sticky, or both.

12. The method of claim 1, wherein the substrate comprises a material having a Young's modulus of between about 1 Pa to about 50 kPa.

13. The method of claim 1, wherein the surface of the substrate being contacted with the surface of the intermediate substrate comprising the composition of interest has a non-planar topography.

14. The method of claim 13, wherein the non-planar topography comprises one selected from the group consisting of an arcuate feature, a curved feature, and a spherical feature.

15. The method of claim 1, wherein the substrate is a sphere, curved surface of a cylinder or curved surface of a cone.

16. The method of claim 1, wherein the surface of the intermediate substrate comprising the composition of interest is placed in conformal contact with the substrate.

17. The method of claim 1, wherein the solubility of the composition of interest in the solvent is lower than the solubility of the intermediate substrate in the solvent.

* * * * *